United States Patent
Wang et al.

(10) Patent No.: US 11,564,651 B2
(45) Date of Patent: Jan. 31, 2023

(54) METHOD AND SYSTEMS FOR ANATOMY/VIEW CLASSIFICATION IN X-RAY IMAGING

(71) Applicant: GE Precision Healthcare LLC, Milwaukee, WI (US)

(72) Inventors: Dejun Wang, Beijing (CN); Jingyi Yang, Beijing (CN); Yaan Ge, Beijing (CN); Aizhen Zhou, Beijing (CN); Katelyn Nye, Glendale, WI (US); Gireesha Rao, Pewaukee, WI (US); Buer Qi, Beijing (CN); Najib Akram, Waukesha, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 404 days.

(21) Appl. No.: 16/742,629

(22) Filed: Jan. 14, 2020

(65) Prior Publication Data
US 2021/0212650 A1 Jul. 15, 2021

(51) Int. Cl.
*G06T 7/30* (2017.01)
*A61B 6/00* (2006.01)
(Continued)

(52) U.S. Cl.
CPC .......... *A61B 6/5217* (2013.01); *A61B 6/5205* (2013.01); *A61B 6/5258* (2013.01);
(Continued)

(58) Field of Classification Search
CPC ............. G06T 7/30; G06T 7/262; G06T 7/35; G06T 7/37; G06T 7/74; G06T 7/0012;
(Continued)

(56) References Cited

U.S. PATENT DOCUMENTS

| 4,903,310 A | 2/1990 | Takeo et al. |
| 5,943,435 A | 8/1999 | Gaborski |

(Continued)

FOREIGN PATENT DOCUMENTS

| CN | 101989326 A | 3/2011 |
| DE | 102015212953 A1 | 1/2017 |

OTHER PUBLICATIONS

Xue, Z. et al., "Chest X-ray Image View Classification," Proceedings of the 2015 IEEE 28th International Symposium on Computer-Based Medical Systems, Jun. 22, 2015, Sao Carlos, Brazil, 6 pages.
Rajkomar, A. et al., "High-Throughput Classification of Radiographs Using Deep Convolutional Neural Networks," Journal of Digital Imaging, vol. 30, No. 1, Feb. 2017, Available Online Oct. 11, 2016, 7 pages.
(Continued)

*Primary Examiner* — Ian L Lemieux
(74) *Attorney, Agent, or Firm* — McCoy Russell LLP (57) ABSTRACT

Various methods and systems are provided for x-ray imaging. In one embodiment, a method for an image pasting examination comprises acquiring, via an optical camera and/or depth camera, image data of a subject, controlling an x-ray source and an x-ray detector according to the image data to acquire a plurality of x-ray images of the subject, and stitching the plurality of x-ray images into a single x-ray image. In this way, optimal exposure techniques may be used for individual acquisitions in an image pasting examination such that the optimal dose is utilized, stitching quality is improved, and registration failures are avoided.

14 Claims, 7 Drawing Sheets

(51) Int. Cl.
*G06K 9/62* (2022.01)
*G06T 3/40* (2006.01)
*G06T 7/70* (2017.01)
*G06V 10/98* (2022.01)

(52) U.S. Cl.
CPC .......... *G06K 9/6267* (2013.01); *G06T 3/4038* (2013.01); *G06T 7/30* (2017.01); *G06T 7/70* (2017.01); *G06V 10/98* (2022.01); *G06T 2207/10116* (2013.01); *G06T 2207/20081* (2013.01); *G06T 2207/20084* (2013.01); *G06T 2207/20221* (2013.01); *G06V 2201/03* (2022.01)

(58) Field of Classification Search
CPC ............. G06T 7/11; G06T 7/149; G06T 7/60; G06T 7/70; G06T 2207/10116; G06T 2207/20081; G06T 2207/20084; G06T 2207/20124; G06T 2207/20221; G06T 2207/30012; G06T 3/4038; G06V 10/40; G06V 10/10; G06V 10/20; G06V 10/98; G06V 2201/03; G06V 40/103; A61B 6/5205; A61B 6/5217; A61B 6/5241; A61B 6/5258; A61B 6/545; G06K 9/00; G06K 9/6267; G06K 9/6289; G06K 9/6292
See application file for complete search history.

(56) References Cited

U.S. PATENT DOCUMENTS

| | | | | |
|---|---|---|---|---|
| 6,895,106 | B2* | 5/2005 | Wang | G01T 1/2014 382/284 |
| 7,375,755 | B2 | 5/2008 | Oya et al. | |
| 7,627,154 | B2* | 12/2009 | Luo | G06V 10/507 382/128 |
| 10,748,319 | B1* | 8/2020 | Tao | G06T 7/33 |
| 10,881,371 | B2* | 1/2021 | Helm | A61B 6/5241 |
| 2007/0242869 | A1 | 10/2007 | Luo et al. | |
| 2013/0034203 | A1* | 2/2013 | Wang | A61B 6/5247 378/62 |
| 2018/0338742 | A1* | 11/2018 | Singh | A61B 6/40 |
| 2020/0405242 | A1* | 12/2020 | Kearney | A61B 6/5217 |
| 2021/0350532 | A1* | 11/2021 | Kimmel | A61B 6/5264 |

OTHER PUBLICATIONS

Szegedy, C. et al., "Inception-v4, Inception-ResNet and Impact of Residual Connections on Learning," Proceedings of the Thirty-First AAAI Conference on Artificial Intelligence (AAAI'17), Feb. 4, 2017, San Francisco, California, 12 pages.

Sandler, M. et al., "MobileNetV2: Inverted Residuals and Linear Bottlenecks," Cornell University arXiv Website, Available Online at https://arxiv.org/abs/1801.04381, Available as Early as Mar. 21, 2019, 14 pages.

* cited by examiner

METHOD AND SYSTEMS FOR ANATOMY/VIEW CLASSIFICATION IN X-RAY IMAGING

FIELD

Embodiments of the subject matter disclosed herein relate to x-ray imaging.

BACKGROUND

Imaging technologies such as x-ray imaging allow for non-invasive acquisition of images of internal structures or features of a subject, such as a patient. Digital x-ray imaging systems produce digital data which can be processed into radiographic images. In digital x-ray imaging systems, radiation from a source is directed toward the subject. A portion of the radiation passes through the subject and impacts a detector. The detector includes an array of discrete picture elements or detector pixels and generates output signals based upon the quantity or intensity of the radiation impacting each pixel region. The output signals are subsequently processed to generate an image that may be displayed for review. These images are used to identify and/or examine the internal structures and organs within a patient's body.

BRIEF DESCRIPTION

In one embodiment, a method comprises controlling an x-ray source and an x-ray detector to acquire an image of a subject, classifying, with a trained neural network, an anatomy/view depicted in the image, performing post-processing of the image based on the anatomy/view, and displaying the post-processed image. In this way, the user workflow for x-ray image acquisition and processing may be simplified, and the consistency in appearance of radiographic images as well as the registration accuracy for image pasting examinations is improved.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of x-ray imaging. In particular, systems and methods are provided for automatic anatomy/view classification for x-ray imaging. An x-ray imaging system, such as the x-ray imaging system depicted in FIG. 1, includes a trained classification network for automatically determining the anatomy/view of an imaging subject. An anatomy/view comprises an orientation and positioning of the imaging subject relative to the x-ray source and x-ray detector. A method for x-ray imaging, such as the method depicted in FIG. 2, includes classifying the anatomy/view depicted in one or more images and post-processing the one or more images based on the anatomy/view. For radiographic image processing, adaptive parameters relating to the overall appearance, such as parameters relating to edge details, contrast, noise level, and so on, are needed for different anatomy/views. A method for radiographic image processing, such as the method depicted in FIGS. 3 and 4, includes automatically adjusting such parameters based on the anatomy/view classified by the classification network. In this way, images are processed with the correct protocol, even if a user of the imaging system selects an incorrect protocol via the imaging system user interface. As the user does not need to select an optimal view protocol for displaying the image, the workflow efficiency is increased while the consistency of displayed images is improved.

Further, image pasting, or the creation of a composite image, is usually accomplished by having a system for acquiring images with a total field-of-view larger than the detector field-of-view (FOV). For applications such as full-spine imaging or long-legs imaging, the total coverage of anatomy (e.g., 60-120 cm) exceeds that of most current detectors and film-screen systems. In one approach to overcome the limitations of the detector FOV, multiple images are acquired during an image pasting examination with overlapping FOVs and stitched together. Historically, images were acquired with the detector FOV, and the various images are then cut manually by a radiologist to avoid overlaps and repasted manually to reconstruct an image with the total FOV. More recently, automatic techniques for digitally pasting successive images have increased the accuracy of image pasting examinations. Often, multiple orientations or views of a subject or patient are acquired during image pasting examinations. In typical workflows for acquiring multiple views of the subject during image pasting examinations, the user selects different protocols for each view. If an incorrect view protocol is selected, the images may be mis-registered for a view, thereby reducing the image pasting accuracy. A method for improving the workflow efficiency and improving the success of image pasting examinations, such as the method depicted in FIGS. 5-7, includes using the classification network to identify the anatomy/view in each image, evaluating the classifications of anatomy/view to ensure that the classifications are correct, and then performing image pasting with appropriate view protocols automatically selected based on the classifications.

Further, in some examples, a camera may be provided in an x-ray imaging system to acquire photographic images in the optical domain. A method for x-ray imaging, such as the method depicted in FIGS. 8 and 9, includes automatically classifying an anatomy/view in camera data acquired with the camera, and automatically selecting an acquisition protocol (e.g., selecting x-ray tube current and/or x-ray tube voltage) based on the anatomy/view of the subject. In this way, appropriate acquisition protocols as well as view protocols may be determined without user input, thereby improving workflow efficiency, increasing the accuracy and consistency of radiographic imaging, and enabling reduced dosage.

Figure 1:
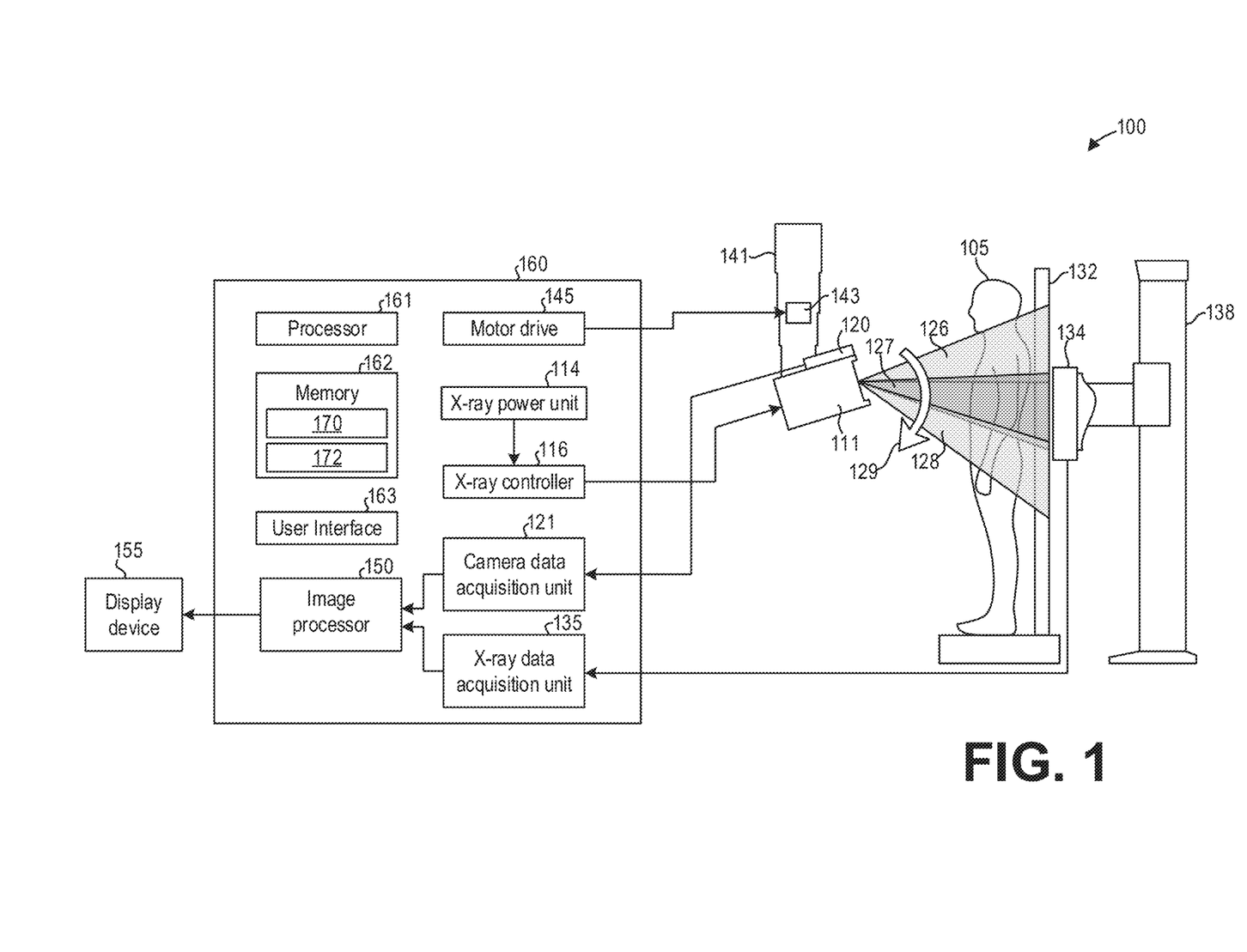
FIG. 1 shows an example x-ray imaging system according to an embodiment.

Turning now to FIG. 1, a block diagram of an x-ray imaging system 100 in accordance with an embodiment is shown. The x-ray imaging system 100 includes an x-ray source 111 which radiates x-rays, a stand 132 upon which the subject 105 stands during an examination, and an x-ray detector 134 for detecting x-rays radiated by the x-ray source 111 and attenuated by the subject 105. The x-ray detector 134 may comprise, as non-limiting examples, a scintillator, one or more ion chamber(s), a light detector array, an x-ray exposure monitor, an electric substrate, and so on. The x-ray detector 134 is mounted on a stand 138 and is configured so as to be vertically moveable according to an imaged region of the subject.

The operation console 160 comprises a processor 161, a memory 162, a user interface 163, a motor drive 145 for controlling one or more motors 143, an x-ray power unit 114, an x-ray controller 116, a camera data acquisition unit 121, an x-ray data acquisition unit 135, and an image processor 150. X-ray image data transmitted from the x-ray detector 134 is received by the x-ray data acquisition unit 135. The collected x-ray image data are image-processed by the image processor 150. A display device 155 communicatively coupled to the operating console 160 displays an image-processed x-ray image thereon.

The x-ray source 111 is supported by a support post 141 which may be mounted to a ceiling (e.g., as depicted) or mounted on a moveable stand for positioning within an imaging room. The x-ray source 111 is vertically moveable relative to the subject or patient 105. For example, one of the one or more motors 143 may be integrated into the support post 141 and may be configured to adjust a vertical position of the x-ray source 111 by increasing or decreasing the distance of the x-ray source 111 from the ceiling or floor, for example. To that end, the motor drive 145 of the operation console 160 may be communicatively coupled to the one or more motors 143 and configured to control the one or more motors 143. The one or more motors 143 may further be configured to adjust an angular position of the x-ray source 111 to change a field-of-view of the x-ray source 111, as described further herein.

The x-ray power unit 114 and the x-ray controller 116 supply power of a suitable voltage current to the x-ray source 111. A collimator (not shown) may be fixed to the x-ray source 111 for designating an irradiated field-of-view of an x-ray beam. The x-ray beam radiated from the x-ray source 111 is applied onto the subject via the collimator.

The x-ray source 111 and the camera 120 may pivot or rotate relative to the support post 141 in an angular direction 129 to image different portions of the subject 105. For example, during an image pasting examination, multiple x-ray images of the subject 105 may be acquired at different angles and pasted or stitched together to form a single image. As depicted, the x-ray source 111 may be oriented with a first field-of-view 126 to acquire a first x-ray image. The x-ray source 111 may then be rotated in the angular direction 129 to a second field-of-view 127 to acquire a second x-ray image. The x-ray source 111 may then be rotated in the angular direction 129 to a third field-of-view 128 to acquire a third x-ray image. The three fields-of-view 126, 127, and 128 are depicted as partially overlapping. The three x-ray images acquired may thus be stitched together as described further herein to form a single x-ray image.

Thus, the x-ray imaging system 100 may be used to perform an image stitching examination as described hereinabove, in addition to performing typical single-energy x-ray image acquisitions.

Such methods, as described further herein, include controlling the processor 161 and/or the image processor 150 to provide an image to a classification network 170 for automatically identifying an anatomy/view depicted in the image. The classification network 170 may comprise a neural network model, such as a convolutional neural network, trained on a set of radiographic images with corresponding labels of the anatomy/view depicted in the images. For example, the classification network 170 may comprise an efficient convolutional neural network such as a MobileNet model. The classification network 170 may be initially trained or primed with a training dataset of large-scale non-radiology images, for example by loading pre-trained parameters obtained by training the neural network with the training dataset of large-scale non-radiology images.

Memory 162 stores executable instructions 172 that when executed cause one or more of the processor 161 and the image processor 150 to perform one or more actions. Example methods that may be stored as the executable instructions 172 are described further herein with regard to FIGS. 2, 3, 5, 6, and 8.

In some examples, the x-ray imaging system 100 may include a camera 120 positioned adjacent to the x-ray source 111 and co-calibrated or co-aligned with the x-ray source 111. The camera 120 may comprise an optical camera that detects electromagnetic radiation in the optical range. Additionally or alternatively, the camera 120 may comprise a depth camera or range imaging camera. As an illustrative and non-limiting example, the camera 120 configured as a depth camera may include an optical camera, an infrared camera, and an infrared projector which projects infrared dots in the field-of-view of the camera 120. The infrared camera images the dots, which in turn may be used to measure depth within the optical camera of the camera 120. As another illustrative and non-limiting example, the camera 120 may comprise a time-of-flight camera. The camera 120 is communicatively coupled to the camera data acquisition unit 121 of the operation console 160. Camera data acquired or generated by the camera 120 may thus be transmitted to the camera data acquisition unit 121, which in turn provides acquired camera image data to the image processor 150 for image processing. The field-of-view of the camera 120 may overlap the field-of-view of the x-ray source 111. In this way, the field-of-view of the x-ray source 111 may be determined automatically from camera data recorded by the camera 120.

Figure 8:
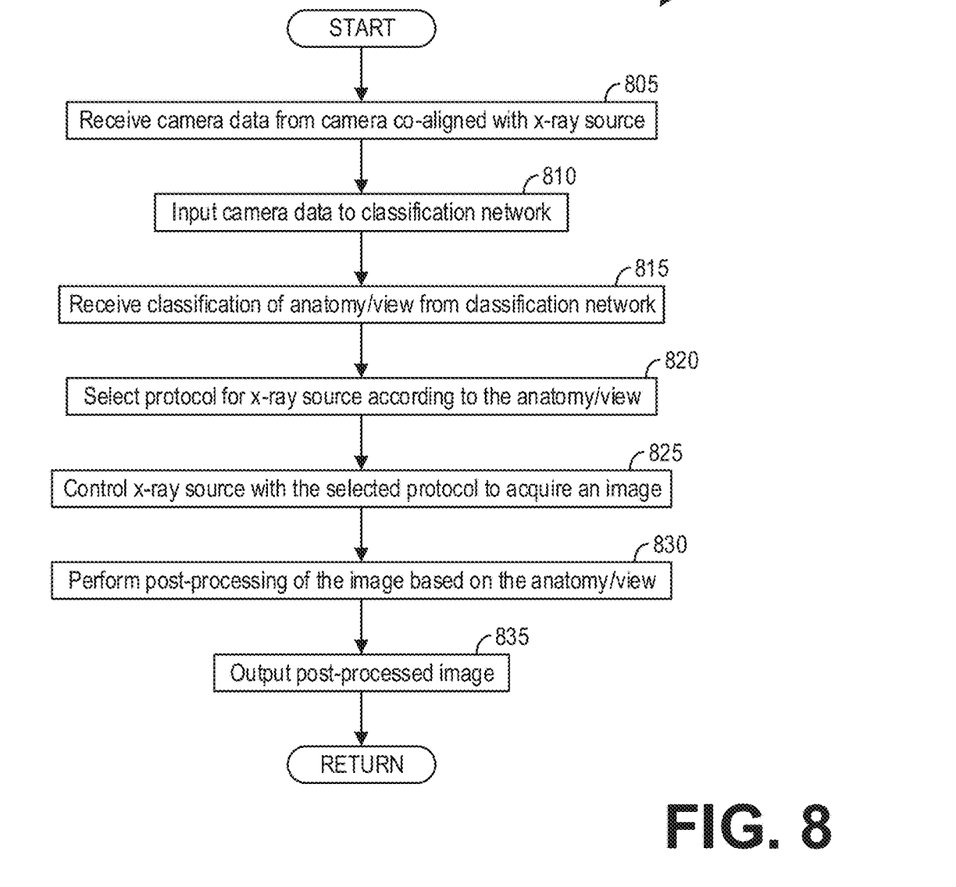
FIG. 8 shows a high-level flow chart illustrating an example method for anatomy/view classification for acquisition protocol selection according to an embodiment.
Figure 9:
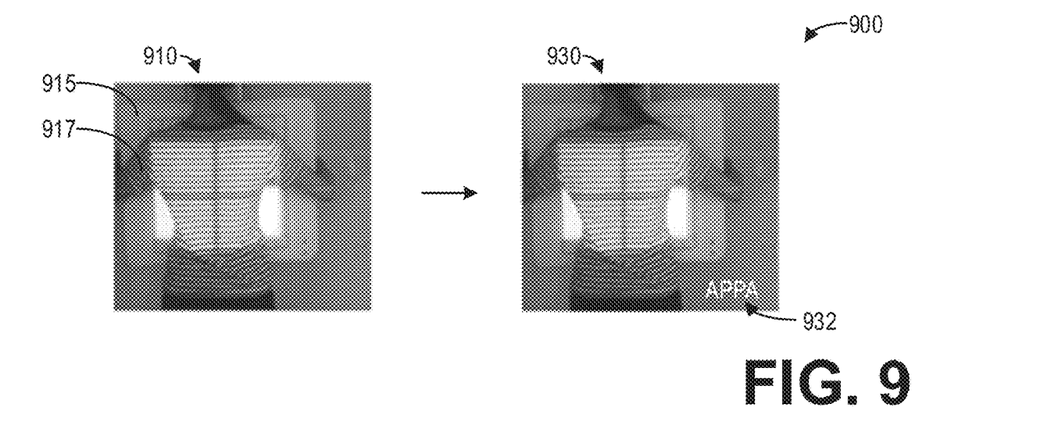
FIG. 9 shows a set of images illustrating anatomy/view classification based on camera data according to an embodiment.

Further, as described further herein with regard to FIGS. 8 and 9, the image processor 150 may process acquired camera data with the classification network 170 to automatically determine the anatomy/view of the subject 105 with respect to the x-ray source 111 and the x-ray detector 134. The image processor 150 may then determine acquisition parameters for controlling the x-ray source 111 and the x-ray detector 134 to acquire one or more radiographic images, as well as view parameters for processing the acquired image(s), based on the anatomy/view determined in the camera data.

Figure 2:
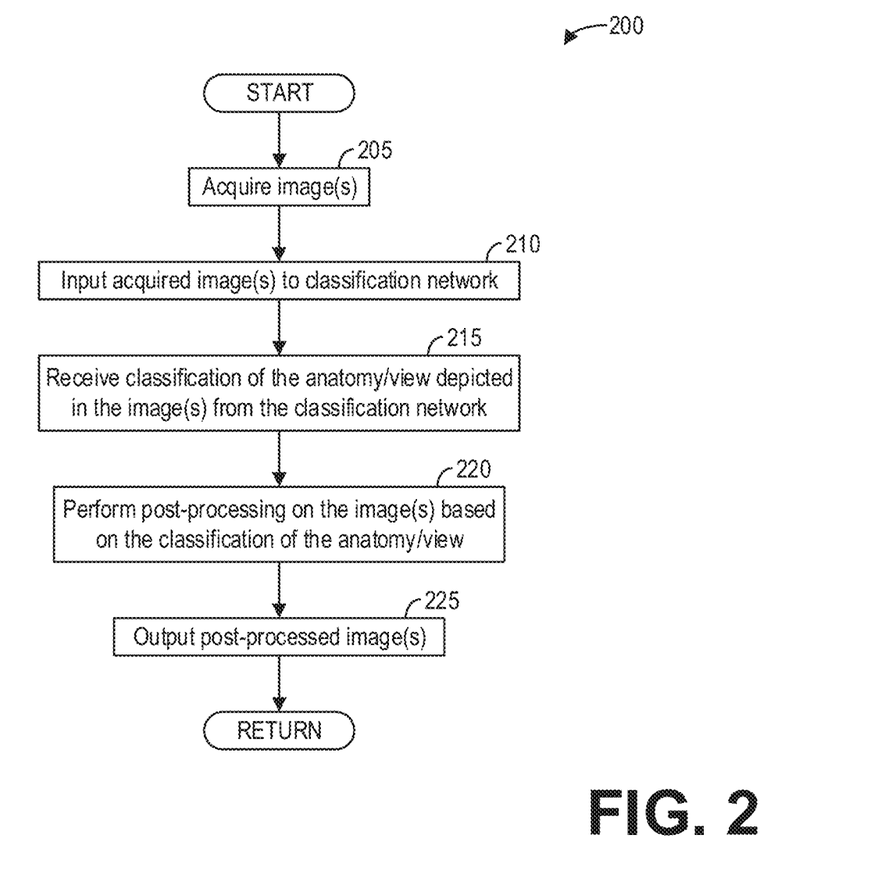
FIG. 2 shows a high-level flow chart illustrating an example method for automatic anatomy/view classification according to an embodiment.

FIG. 2 shows a high-level flow chart illustrating an example method 200 for automatic anatomy/view classification according to an embodiment. In particular, method 200 relates to automatically classifying the anatomy/view depicted in one or more images with a classification network, such as the classification network 170. Method 200 is described with regard to the systems and components of FIG. 1, though it should be appreciated that the method 200 may be implemented with other systems and components without departing from the scope of the present disclosure. Method 200 may be stored as executable instructions 172 in the non-transitory memory 162 of the operation console 160, for example, and may be executed by one or more of the processor 161 and the image processor 150 to perform the actions described herein below.

Method 200 begins at 205. At 205, method 200 acquires one or more images. In some examples, method 200 may control the x-ray source 111 to generate a beam of x-rays towards the x-ray detector 134, and converts the x-rays detected by the x-ray detector 134 to a radiographic image. In other examples, method 200 controls the x-ray source 111 and the x-ray detector 134 to acquire a series of radiographic images, while adjusting the relative position of the x-ray source 111 and the x-ray detector 134 such that the radiographic images depict different but adjacent regions of the subject 105. In such examples, method 200 may control the x-ray source 111 and the x-ray detector 134 to acquire multiple images of the subject 105 in different views. For example, method 200 may acquire two or more of an image of the subject 105 with a right lateral view, an image of the subject 105 with an anterior-posterior (AP) view, an image of the subject 105 with a posterior-anterior (PA) view, and an image of the subject 105 with a left lateral view. As another example, method 200 may acquire multiple images in multiple views of the subject 105, wherein the multiple images depict different but adjacent regions of the subject 105.

After acquiring the image(s) at 205, method 200 continues to 210. At 210, method 200 inputs the acquired image(s) to a classification network, such as the classification network 170. The classification network 170 is trained to classify an anatomy/view depicted in the acquired image(s). For example, the anatomy may comprise a head, spine, abdomen, leg, and so on, while the view may indicate an orientation of the subject with respect to the x-ray detector, expressed in anatomical terms, such as lateral, anterior-posterior (AP), posterior-anterior (PA), and so on. The anatomy/view classified by the classification network may thus be output as a combination of the anatomy depicted in the image as well as the view of the anatomy depicted in the image. For example, the output of the classification network 170 may comprise an anatomy/view classification such as Spine APPA, Spine Right Lateral, Spine Left Lateral, Leg APPA, and so on.

Continuing at 215, method 200 receives a classification of the anatomy/view depicted in the one or more acquired image(s) from the classification network 170. That is, for each acquired image input to the classification network 170, method 200 receives a corresponding anatomy/view classification. For example, if a single radiographic image is acquired at 205, method 200 receives a classification of the anatomy/view depicted in the single radiographic image. If a series of radiographic images are acquired at 205 for image pasting, then method 200 receives a classification of the anatomy/view depicted in each radiographic image in the series.

At 220, method 200 performs post-processing on the one or more acquired image(s) based on the classification of the anatomy/view. For example, based on the classification of the anatomy/view in an image, method 200 selects post-processing parameters according to the classification for post-processing the image, as different post-processing preferences regarding edge details, contrast, noise level, and so on may be used for different anatomy/views. Therefore, a post-processing protocol comprising a set of post-processing parameters may be configured for each anatomy/view, and method 200 may select the appropriate post-processing protocol based on the classification. Method 200 then processes the acquired image according to the post-processing protocol or according to the post-processing parameters selected based on the anatomy/view classification. In this way, the automatic classification of the anatomy/view enables the automatic selection of the correct parameters for post-processing of images, thereby ensuring a consistent appearance for the user.

As another example, for multiple images acquired in a view, the post-processing of the acquired images may include post-processing of the contrast, edge details, noise level, and so on as mentioned hereinabove for a single image, and may further include image pasting or image stitching. That is, in some examples, the post-processing of the acquired images may include stitching the multiple images together into a single image with a larger field-of-view than the field-of-view of each individual image. In order to ensure that the correct images are stitched in accordance with the correct protocol, method 200 automatically selects the protocol for stitching the images based on the anatomy/view classification for each image. In this way, the image pasting registration success rate is improved while eliminating the need for the user to manually select the protocol for each view.

At 225, method 200 outputs the post-processed image(s). Method 200 may output the post-processed image(s), for example, to the display device 155 for display to the user. In addition, method 200 may output the post-processed image(s) to the memory 162 for later review, and/or to a picture archiving and communication system (PACS). After outputting the post-processed image(s), method 200 then returns.

Figure 3:
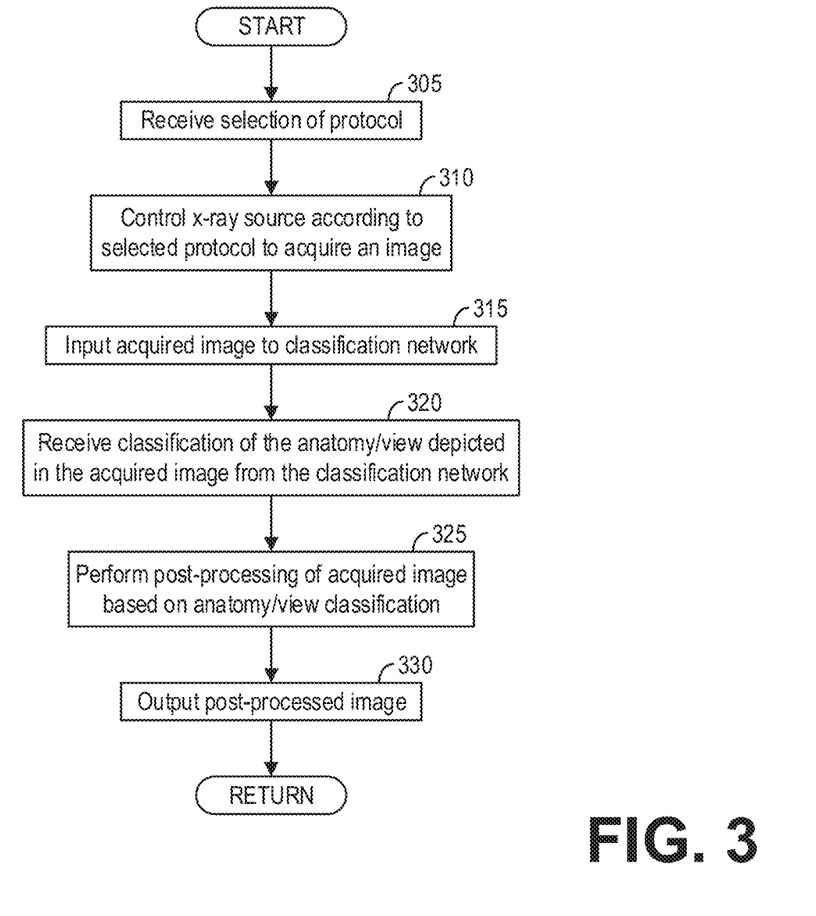
FIG. 3 shows a high-level flow chart illustrating an example method for post-processing of an acquired radiographic image based on an anatomy/view classification according to an embodiment.

FIG. 3 shows a high-level flow chart illustrating an example method 300 for post-processing of an acquired radiographic image based on an anatomy/view classification according to an embodiment. In particular, method 300 relates to automatically selecting parameters for post-processing of an acquired image based on an automatically classified anatomy/view depicted in the acquired image. Method 300 is described with regard to the systems and components of FIG. 1, though it should be appreciated that the method 300 may be implemented with other systems and components without departing from the scope of the present disclosure. Method 300 may be stored as executable instructions 172 in the non-transitory memory 162 of the operation console 160, for example, and may be executed by one or more of the processor 161 and the image processor 150 to perform the actions described herein below.

Method 300 begins at 305. At 305, method 300 receives a selection of a protocol. Method 300 specifically receives a selection of an acquisition protocol specifying one or more parameters for acquiring an image, such as tube voltage, tube current, and so on. Method 300 may receive the selection of the protocol, for example, via the user interface 163. Continuing at 310, method 300 controls an x-ray source, such as the x-ray source 111, according to the selected protocol to acquire an image. Method 300 may further control an x-ray detector, such as the x-ray detector 134, to acquire the image in accordance with the protocol.

After acquiring the image, method 300 continues to 315. At 315, method 300 inputs the acquired image to a classification network, such as the classification network 170. As discussed hereinabove, the classification network 170 is trained to classify an anatomy/view depicted in the acquired image. For example, the anatomy may comprise a head, spine, abdomen, leg, and so on, while the view may indicate an orientation of the subject with respect to the x-ray detector, expressed in anatomical terms, such as lateral, anterior-posterior (AP), posterior-anterior (PA), and so on. The anatomy/view classified by the classification network may thus be output as a combination of the anatomy depicted in the image as well as the view of the anatomy depicted in the image. For example, the output of the classification network 170 may comprise an anatomy/view classification such as Spine APPA, Spine Right Lateral, Spine Left Lateral, Leg APPA, and so on.

Thus, continuing at 320, method 300 receives a classification of the anatomy/view depicted in the acquired image from the classification network 170. At 325, method 300 performs post-processing of the acquired image based on the anatomy/view classification. For example, based on the classification of the anatomy/view in an image, method 300 selects post-processing parameters according to the classification for post-processing the image, as different post-processing preferences regarding edge details, contrast, noise level, and so on may be used for different anatomy/views. Therefore, a post-processing protocol comprising a set of post-processing parameters may be configured for each anatomy/view, and method 300 may select the appropriate post-processing protocol based on the classification. Method 300 then processes the acquired image according to the post-processing protocol, or according to the post-processing parameters selected based on the anatomy/view classification. In this way, the automatic classification of the anatomy/view enables the automatic selection of the correct parameters for post-processing of images, thereby ensuring a consistent appearance for the user.

At 330, method 300 outputs the post-processed image. For example, method 300 may output the post-processed image to the display device 155 for display to the user. Additionally, method 300 may output the post-processed image to the memory 162 for storage, and/or a PACS for remote storage and/or review. Method 300 then returns.

Figure 4:
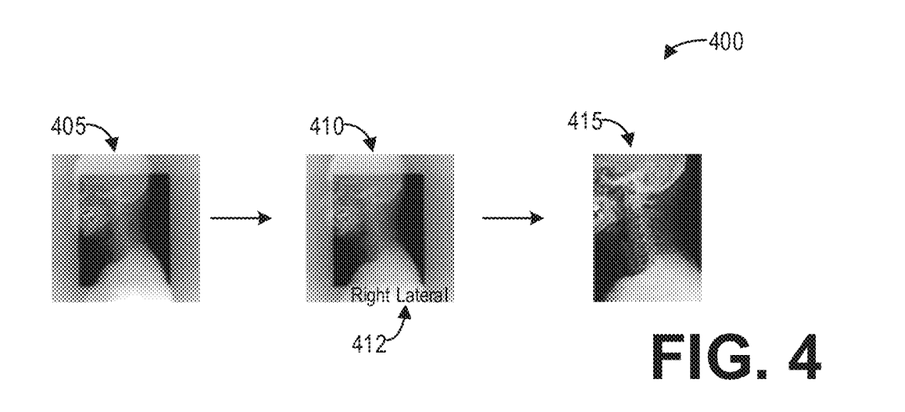
FIG. 4 shows a set of images illustrating the method of FIG. 3 according to an embodiment.

As an illustrative example, FIG. 4 shows a set of images 400 illustrating the automatic classification of an acquired image. The set of images 400 includes an example acquired image 405. The set of images 400 further includes an example output 410 of the classification network including the acquired image 405 and the anatomy/view classification 412 for the acquired image 405. As depicted, the anatomy/view classification 412 indicates that the view of the acquired image 405 is a "Left Lateral" view. In some examples, the anatomy/view classification 412 may be superimposed on the acquired image 405 and displayed to the user, for example via the display device 155, for confirmation. In other examples, the anatomy/view classification 412 may not be superimposed on the acquired image 405 or displayed to the user. Further, while the anatomy/view classification 412 as depicted does not explicitly indicate the anatomy, in some examples the anatomy/view classification 412 may further explicitly indicate the anatomy, for example by indicating the "Neck" anatomy in addition to the "Left Lateral" view in the anatomy/view classification 412. As discussed hereinabove, the acquired image 405 is post-processed according to the anatomy/view classification 412. In particular, one or more post-processing parameters including but not limited to the field-of-view, contrast, edge details, noise reduction, and so on may be determined based on the anatomy/view classification 412, and the acquired image 405 may be processed according to the one or more post-processing parameters to generate the post-processed image 415. In this way, the workload of manually selecting a post-processing or view protocol may be relieved while maintaining a high-quality post-processing performance.

Figure 5:
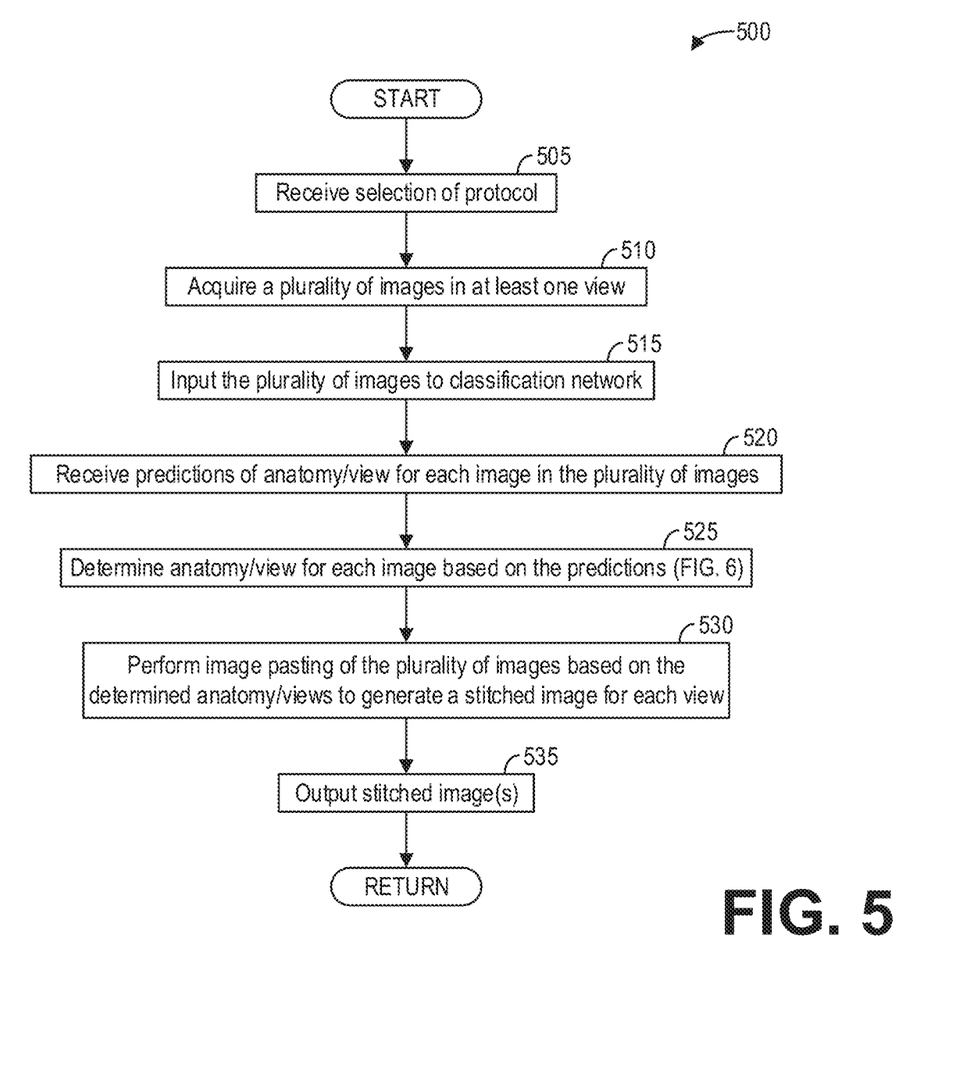
FIG. 5 shows a high-level flow chart illustrating an example method for image pasting of radiographic images based on anatomy/view classifications according to an embodiment.

FIG. 5 shows a high-level flow chart illustrating an example method 500 for image pasting of radiographic images based on anatomy/view classifications according to an embodiment. In particular, method 500 relates to acquiring multiple images in at least one view and automatically post-processing the multiple images based on an automatic anatomy/view classification to obtain at least one stitched image. Method 500 is described with regard to the systems and components of FIG. 1, though it should be appreciated that the method 500 may be implemented with other systems and components without departing from the scope of the present disclosure. Method 500 may be stored as executable instructions 172 in the non-transitory memory 162 of the operation console 160, for example, and may be executed by one or more of the processor 161 and the image processor 150 to perform the actions described herein below.

Method 500 begins at 505. At 505, method 500 receives a selection of a protocol. Method 500 specifically receives a selection of an acquisition protocol specifying one or more parameters for acquiring an image, such as tube voltage, tube current, and so on. The acquisition protocol may comprise an image pasting acquisition protocol, and thus may include a definition of patient coverage. The acquisition protocol may correspond to a specific view. For example, the acquisition protocol may comprise an APPA acquisition protocol or a lateral acquisition protocol. Furthermore, the acquisition protocol may specify an anatomy to be imaged, such that appropriate acquisition parameters may be selected. Method 500 may receive the selection of the protocol, for example, via the user interface 163.

At 510, method 500 acquires a plurality of images in at least one view. To that end, method 500 controls the x-ray source 111 and the x-ray detector 134, for example, according to the protocol selected at 505, to acquire a series of radiographic images, while adjusting the relative position of the x-ray source 111 and the x-ray detector 134 such that the radiographic images depict different but adjacent regions of the subject 105. In such examples, method 500 may control the x-ray source 111 and the x-ray detector 134 to acquire multiple images of the subject 105 in a first view (e.g., APPA, lateral, and so on) as well as a second view different from the first view.

After acquiring the plurality of images, method 500 continues to 515. At 515, method 500 inputs the plurality of images to a classification network, such as the classification network 170. As discussed hereinabove, the classification network 170 is trained to classify an anatomy/view depicted in the acquired images. For example, the anatomy may comprise a head, spine, abdomen, leg, and so on, while the view may indicate an orientation of the subject with respect to the x-ray detector, expressed in anatomical terms, such as lateral, anterior-posterior (AP), posterior-anterior (PA), and so on. The anatomy/view classified by the classification network may thus be output as a combination of the anatomy depicted in an image as well as the view of the anatomy depicted in the image. For example, the output of the classification network 170 may comprise an anatomy/view classification such as Spine APPA, Spine Right Lateral, Spine Left Lateral, Leg APPA, and so on. Thus, at 520, method 500 receives predictions of the anatomy/view for each image in the plurality of images. That is, the classification network 170 outputs a classification of the anatomy/view for each image, along with a prediction or a probability regarding how likely the anatomy/view classification for each image is correct.

Continuing at 525, method 500 determines the anatomy/view for each image based on the predictions. As described further herein with regard to FIG. 6, a method for determining the anatomy/view for each image based on the prediction of the anatomy/view classification output by the classification network 170 includes evaluating each of the predictions according to one or more conditions to ensure that the images are accurately classified. Thus, in some examples, method 500 may determine that the anatomy/view classification for each image predicted by the classification network 170 is correct. Meanwhile, in other examples, method 500 may adjust an anatomy/view classification of a first image from a first view to a second view, for example, if a second image is predicted to the same anatomy/view classification as the first image while also having a higher probability of belonging to that anatomy/view classification, and if none of the images were classified by the classification network 170 to the second view at the corresponding anatomy. That is, method 500 may automatically and accurately deduce the appropriate anatomy/view classifications, even in instances of redundant anatomy/view classifications.

After determining the anatomy/view classifications for each image in the plurality of images, method 500 continues to 530. At 530, method 500 performs image pasting of the plurality of images based on the determined anatomy/views to generate a stitched image for each view. In some examples, method 500 may process each of the images according to the respective anatomy/view classifications with post-processing parameters selected according to the anatomy/view classifications. Further, method 500 selects an image pasting protocol for each view to apply to the plurality of images determined to correspond to the view, and then performs image pasting of the plurality of images according to the image pasting protocol. Thus, images in a lateral view may be automatically stitched according to a lateral image pasting protocol, while images in an anterior-posterior view may be automatically stitched according to an anterior-posterior image pasting protocol. By using the correct image pasting protocol, the registration of the images within the view is improved.

At 535, method 500 outputs the stitched image(s). For example, method 500 may output the stitched image for each view to the display device 155 for display, and additionally may output the stitched image(s) to the memory 162 and/or a PACS. Method 500 then returns.

Figure 6:
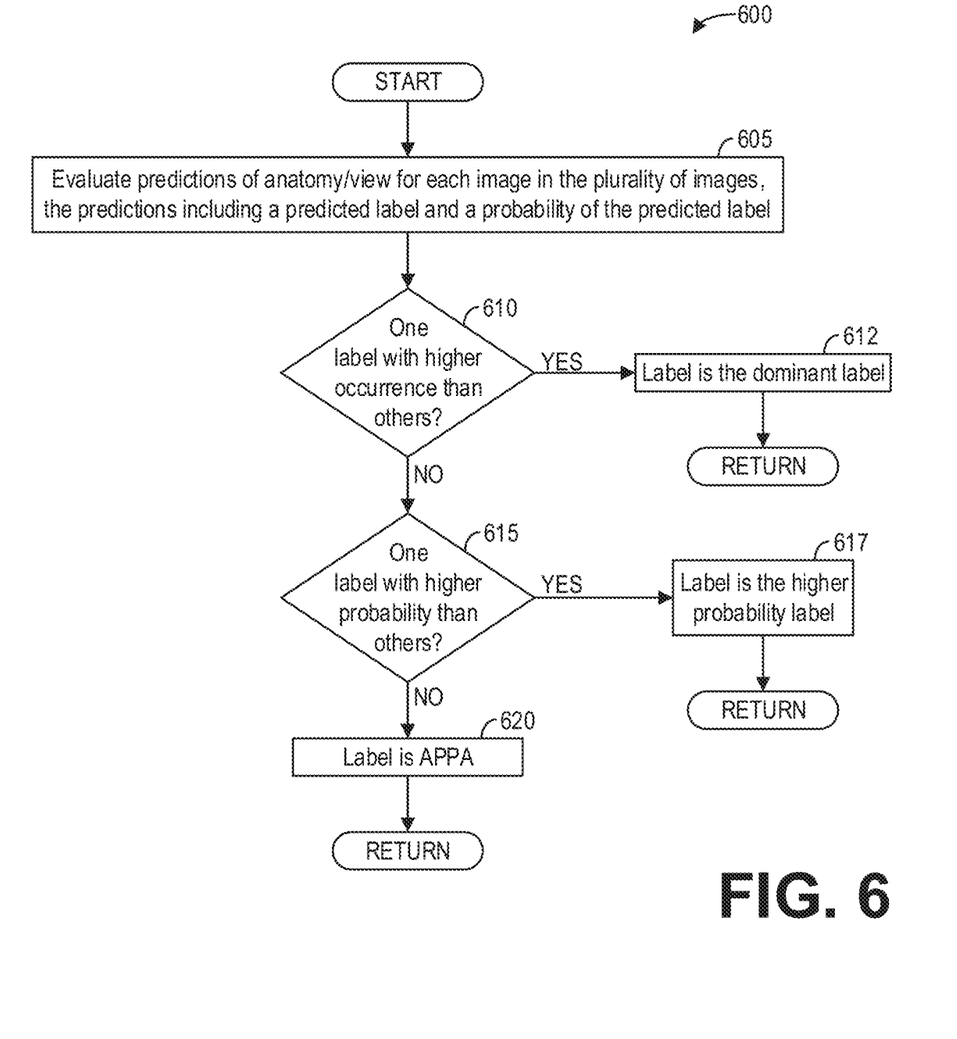
FIG. 6 shows a high-level flow chart illustrating an example method for determining anatomy/view classifications based on predictions of anatomy/view classifications for multiple radiographic images according to an embodiment.

FIG. 6 shows a high-level flow chart illustrating an example method 600 for determining anatomy/view classifications based on predictions of anatomy/view classifications for multiple radiographic images according to an embodiment. In particular, method 600 may comprise a sub-routine of method 500, for example by comprising the action 525 described hereinabove. Method 600 specifically relates to determining an appropriate label for a plurality of images acquired in a view, wherein the label corresponds to the view, and so if multiple views are acquired during execution of method 500, method 600 may be executed for each plurality of images acquired in each view. Method 600 is therefore described with regard to the systems and components of FIG. 1 as well as the method 500 of FIG. 5, though it should be appreciated that the method 600 may be implemented with other systems, components, and methods without departing from the scope of the present disclosure. Method 600 may be stored as executable instructions 172 in the non-transitory memory 162 of the operation console 160, for example, and may be executed by one or more of the processor 161 and the image processor 150 to perform the actions described herein below.

Method 600 begins at 605. At 605, method 600 evaluates the predictions of the anatomy/view for each image in the plurality of images, the predictions including a predicted label (e.g., Left Lateral, Right Lateral, APPA, and so on) and a probability of the predicted label. At 610, method 600 determines whether a first condition is satisfied. In particular, method 600 determines whether there is a predicted label in the predictions with a higher occurrence than others. For example, if the predictions for two images out of three images are for a Left Lateral view, while the prediction for the third image is for Right Lateral view, then the Left Lateral predicted label has a higher occurrence than the Right Lateral predicted label. In this example, the first condition is satisfied. Similarly, if the predictions for all images include the same predicted label, then the predicted label has the highest occurrence, and the first condition is satisfied. In contrast, if an equal number of predictions are for a first predicted label as well as for a second predicted label, then there is no predicted label with a highest occurrence and the first condition is not satisfied.

If the first condition is satisfied ("YES"), method 600 continues to 612, wherein method 600 classifies the anatomy/view according to the predicted label with the higher occurrence. That is, all of the images in the plurality of images are classified according to the predicted label with the higher occurrence. Method 600 then returns.

However, if the first condition is not satisfied ("NO") at 610, method 600 continues to 615. At 615, method 600 determines whether a second condition is satisfied. In particular, method 600 determines whether there is one predicted label with a higher probability than the other predicted labels. For example, if half of the images are predicted to a first label with a first probability, and the other half of the images are predicted to a second label with a second probability, method 600 determines whether the first probability is higher than the second probability. If one of the probabilities is higher than the other(s), then the second condition is satisfied ("YES"), and method 600 continues to 617, wherein method 600 determines that label is the predicted label with the higher probability, and classifies the anatomy/view for the plurality of images according to the predicted label with the higher probability. Method 600 then returns.

However, if the second condition is not satisfied ("NO") at 615, method 600 continues to 620. As a particular anatomy/view in the predictions is not clearly dominant in the predictions, then the anatomy/view is most likely APPA.

Thus, at 620, method 600 concludes that the label corresponds to APPA and classifies the anatomy/view as APPA for all images in the plurality of images. Method 600 then returns.

As an illustrative example, consider a set of images wherein the prediction for a first image is Right Lateral with a probability of 0.553, while the prediction for a second image is Left Lateral with a probability of 1. According to method 600, the predictions for the set of images does not satisfy the first condition, since there is an equal occurrence of predicted labels Right Lateral and Left Lateral. However, since the probability for the second image predicted to Left Lateral is higher than the probability of the first image predicted to Right Lateral, the second condition is satisfied and both images are classified as Left Lateral.

Figure 7:
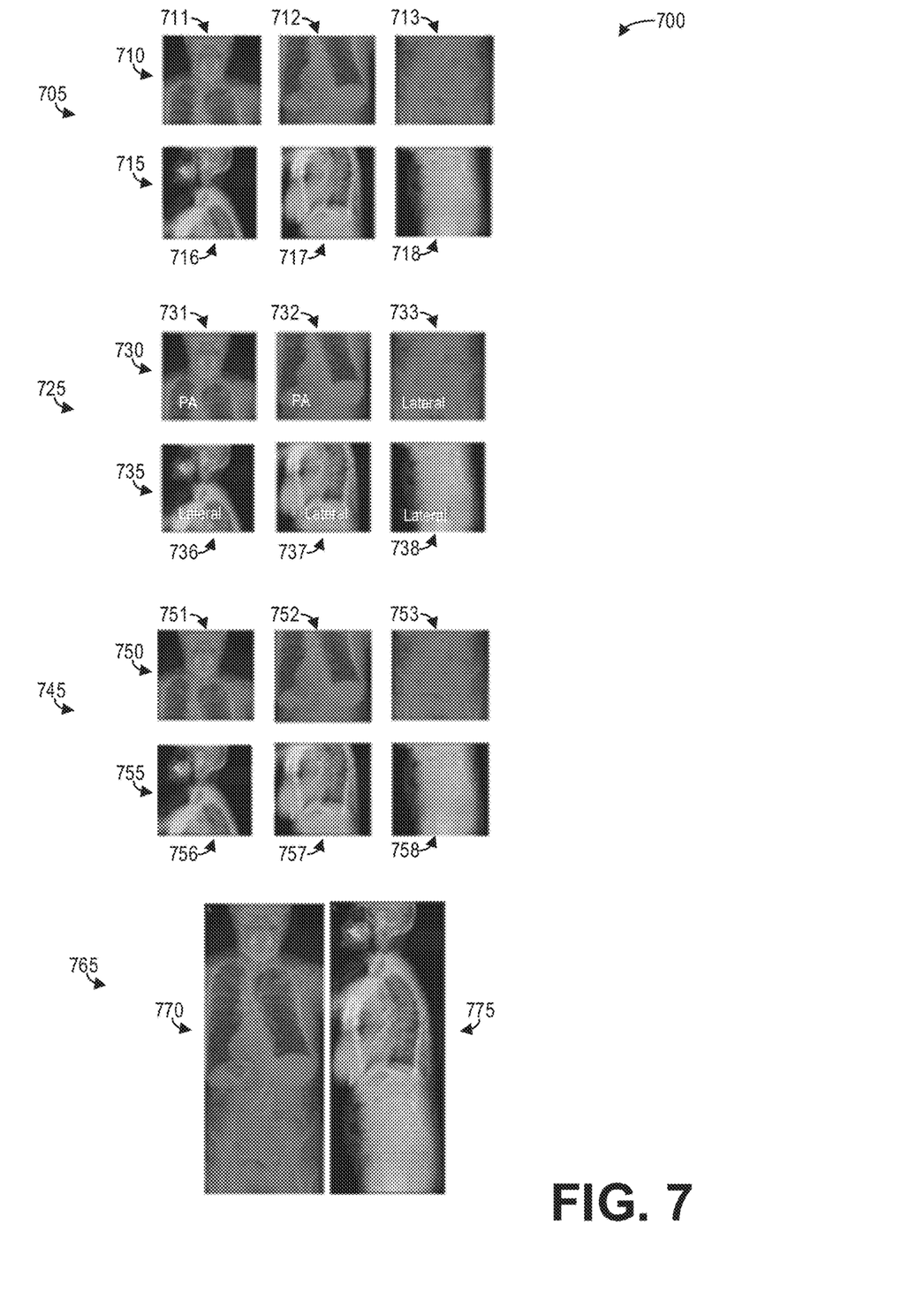
FIG. 7 shows a set of images illustrating the method of FIG. 5 according to an embodiment.

To illustrate the image pasting methods provided herein, FIG. 7 shows a set of example images 700 illustrating the method 500 of FIG. 5 according to an embodiment. The set of example images 700 includes a plurality of acquired images 705. The acquired images 705 include a first set 710 of images and a second set 715 of images, wherein the first set 710 includes a first image 711, a second image 712, and a third image 713, while the second set 715 includes a fourth image 715, a fifth image 716, and a sixth image 717. As depicted, the first set 710 of images is acquired for a first view, in particular a PA view, while the second set 715 of images is acquired for a second view different from the first view, in particular a lateral view. The plurality of acquired images 705 are input to a classification network, such as the classification network 170, to automatically determine an anatomy/view classification for each image in the plurality of acquired images 705.

As depicted, the classification network 170 outputs a set of predictions 725 for the acquired images 705, including a first set 730 of predictions and a second set 735 of predictions. The first set 730 of predictions includes a first prediction 731 for the first image 711, a second prediction 732 for the second image 712, and a third prediction 733 for the third image 713 of the first set 710 of images. The second set 735 of predictions includes a fourth prediction 736 for the fourth image 716, a fifth prediction 737 for the fifth image 717, and a sixth prediction 738 for the sixth image 718 of the second set 715.

In particular, the first prediction 731 indicates that the first image 711 is a PA view, the second prediction 732 indicates that the second image 712 is a PA view, and the third prediction 733 indicates that the third image 713 is a lateral view. Meanwhile, the fourth prediction 736 indicates that the fourth image 716 is a lateral view, the fifth prediction 737 indicates that the fifth image 717 is a lateral view, and the sixth prediction 738 indicates that the sixth image 718 is a lateral view.

As both the third prediction 733 and the sixth prediction 738 indicate that the third image 713 and the sixth image 738 correspond to a lateral view with a same anatomy, such that more images are classified to the lateral view than the PA view, the set of predictions 725 is evaluated as described hereinabove with regard to FIGS. 5 and 6 to determine the appropriate anatomy/view classification for each image. That is, method 600 is applied separately to the first set 730 of predictions and the second set 735 of predictions. In the first set 730, the occurrence of the PA anatomy/view prediction is higher than the occurrence of the Lateral anatomy/view prediction, and so the third prediction 733 is re-classified to a PA anatomy/view.

Thus, after applying the decision algorithm of FIG. 6, the classified sets 745 are obtained, wherein the first classified set 750 is definitively classified to the PA view while the second classified set 755 is definitively classified to the lateral view. In particular, the first classified set 750 includes a first image 751, a second image 752, and a third image 753 determined as comprising a first view, in particular the PA view. The first image 751, the second image 752, and the third image 753 correspond respectively to the first image 711, the second image 712, and the third image 713 of the first set 710

The second classified set 755 includes a fourth image 756, a fifth image 757, and a sixth image 758 determined as comprising a second view, in particular the lateral view. The fourth image 756, the fifth image 757, and the sixth image 758 correspond respectively to the fourth image 716, the fifth image 717, and the sixth image 718 of the second set 715 of images.

The classified images 745 are then image pasted or stitched to obtain the pasted images 765. In particular, the first classified set 750 of images are stitched according to a PA image pasting protocol to obtain the first pasted image 770, while the second classified set 755 of images are stitched according to a lateral image pasting protocol to obtain the second pasted image 775. By using the appropriate image pasting protocol to stitch the classified images 745, the accuracy of the registration of the classified images 745 is improved, and consequently the classified images 745 are accurately stitched to generate the pasted images 765.

Thus, methods and systems are provided for improving the post-processing of one or more acquired images that includes automatically classifying the anatomy/view depicted in the one or more acquired images.

In some examples, an x-ray imaging system such as the x-ray imaging system 100 may include a camera, such as the camera 120, co-aligned with the x-ray source 111 to capture camera data of the subject 105. In such examples, a classification network such as the classification network 170 may be trained to automatically classify the anatomy/view depicted in such camera data. As a result, an appropriate acquisition protocol may be automatically selected prior to acquiring an x-ray image, without manual input from a user of the x-ray imaging system 100.

As an illustrative example, FIG. 8 shows a high-level flow chart illustrating an example method 800 for anatomy/view classification for acquisition protocol selection according to an embodiment. In particular, method 800 relates to classifying an anatomy/view based on camera data, and then acquiring an x-ray image based on the classified anatomy/view. Method 800 is described with regard to the systems and components of FIG. 1, though it should be appreciated that the method 800 may be implemented with other systems and components without departing from the scope of the present disclosure. Method 800 may be stored as executable instructions 172 in the non-transitory memory 162 of the operation console 160, for example, and may be executed by one or more of the processor 161 and the image processor 150 to perform the actions described herein below.

Method 800 begins at 805. At 805, method 800 receives camera data from a camera, such as the camera 120, co-aligned with an x-ray source, such as the x-ray source 111. The camera data comprises optical or non-radiographic images of the subject 105, for example. As the camera 120 is co-aligned with the x-ray source 111, the camera data thus captured depicts the orientation of the subject 105 relative to the x-ray source 111 and the x-ray detector 134. Continuing at 810, method 800 inputs the camera data to a classification network, such as the classification network 170. As discussed hereinabove, the classification network 170 is trained to classify an anatomy/view depicted in acquired images. In addition to classifying the anatomy/view depicted in radiographic images as described hereinabove, the classification network 170 may further be trained to classify the anatomy/view depicted in camera data. For example, the anatomy may comprise a head, spine, abdomen, leg, and so on, while the view may indicate an orientation of the subject with respect to the x-ray detector, expressed in anatomical terms, such as lateral, anterior-posterior (AP), posterior-anterior (PA), and so on. The anatomy/view classified by the classification network may thus be output as a combination of the anatomy depicted in the camera data as well as the view of the anatomy depicted in the camera data. For example, the output of the classification network 170 may comprise an anatomy/view classification such as Spine APPA, Spine Right Lateral, Spine Left Lateral, Leg APPA, and so on.

At 815, method 800 receives a classification of the anatomy/view depicted in the camera data from the classification network. Continuing at 820, method 800 selects a protocol for the x-ray source 111 according to the anatomy/view classification. For example, method 800 automatically selects one or more acquisition parameters based on the anatomy/view classification. Then, at 825, method 800 controls the x-ray source 111 with the selected protocol to acquire an x-ray or radiographic image. Further, since the anatomy/view is already classified based on the camera data, it is unnecessary to classify the anatomy/view in the acquired x-ray image with the classification network 170. Thus, continuing at 830, method 800 performs post-processing of the acquired image based on the anatomy/view classification as described hereinabove. At 835, method 800 outputs the post-processed image, for example, to the display device 155 for display to the user. Method 800 may also output the post-processed image to the memory 162 for storage and/or a PACS. Method 800 then returns.

FIG. 9 shows a set of images 900 illustrating anatomy/view classification based on camera data according to an embodiment. The set of images 900 includes a camera image 910 acquired via a camera, such as camera 120, co-aligned with an x-ray source, such as x-ray source 111. The camera image 910 depicts an imaging subject 917 positioned in front of the detector 915, which may comprise the detector 134 of FIG. 1. The camera image 910, also referred to hereinabove as camera data, is input to the classification network 170 to automatically classify the anatomy/view of the camera image 910. The output 930 of the classification network 170 includes the camera image 910 as well as a label or classification 932 of the anatomy/view determined by the classification network 170. As depicted, the classification 932 output by the classification network 170 indicates that the view corresponds to an APPA view. It should be appreciated that, while not explicitly depicted in FIG. 9, the classification 932 may further indicate an anatomy depicted in the camera data 910, such as Spine or Torso. As described hereinabove, the classification 932 may be used to automatically select an acquisition protocol for controlling the x-ray source 111 and the x-ray detector 134 to acquire one or more radiographic images. Furthermore, the classification 932 may also be used to determine view or post-processing parameters for post-processing the acquired radiographic images. Thus, by including a camera 120 in the x-ray imaging system 100 as well as the classification network 170, the user may be relieved from selecting the acquisition protocol and/or the view or post-processing protocol.

A technical effect of the disclosure includes a classification of an anatomy and a view depicted in an image. Another technical effect of the disclosure includes the automatic selection of an acquisition protocol and/or a post-processing protocol according to an anatomy and a view. Yet another technical effect of the disclosure includes the improved registration between images in an image pasting examination. Another technical effect of the disclosure includes the accurate processing of acquired radiographic images according to automatically classified anatomies and views depicted in the acquired radiographic images.

In one embodiment, a method comprises controlling an x-ray source and an x-ray detector to acquire an image of a subject, classifying, with a trained neural network, an anatomy/view depicted in the image, performing post-processing of the image based on the anatomy/view, and displaying the post-processed image.

In a first example of the method, the method further comprises determining parameters for adjusting one or more of edge details, contrast, and noise level in the image according to the anatomy/view, and performing the post-processing of the image according to the determined parameters. In a second example of the method optionally including the first example, the method further comprises controlling the x-ray source and the x-ray detector to acquire a plurality of images of the subject including the image and at least a second image, wherein the image and the second image depict adjacent and overlapping regions of the subject. In a third example of the method optionally including one or more of the first and second examples, the method further comprises classifying, with the trained neural network, anatomy/views depicted in the plurality of images, including at least a second anatomy/view depicted in the second image. In a fourth example of the method optionally including one or more of the first through third examples, performing the post-processing of the image based on the anatomy/view comprises registering the plurality of images according to the anatomy/views depicted in the plurality of images, including registering the image to the second image according to the anatomy/view and the second anatomy/view, and stitching the registered plurality of images to generate a stitched image, wherein displaying the post-processed image comprises displaying the stitched image. In a fifth example of the method optionally including one or more of the first through fourth examples, registering the plurality of images according to the anatomy/views depicted in the plurality of images, including registering the image to the second image according to the anatomy/view and the second anatomy/view, comprises determining that the anatomy/views including the anatomy/view and the second anatomy/view comprise a same, first anatomy/view, and registering the plurality of images according to an image pasting protocol configured for the first anatomy/view. In a sixth example of the method optionally including one or more of the first through fifth examples, the method further comprises controlling the x-ray source and the x-ray detector to acquire a second plurality of images including at least a third image and a fourth image of the subject, wherein the plurality of images including the image and at least the second image depict adjacent and overlapping regions of the subject in a first view corresponding to the first anatomy/view, and wherein the second plurality of images depict adjacent and overlapping regions of the subject in a second view different from the first view. In a seventh example of the method optionally including one or more of the first through sixth examples, the method further comprises classifying, with the trained neural network, anatomy/views depicted in the second plurality of images including a third anatomy/view depicted in the third image and a fourth anatomy/view depicted in the fourth image. In an eighth example of the method optionally including one or more of the first through seventh examples, the method further comprises determining that the anatomy/views depicted in the second plurality of images comprise an anatomy/view corresponding to the second view, registering the second plurality of images according to an image pasting protocol for the anatomy/view corresponding to the second view, stitching the registered second plurality of images to generate a second stitched image with the second view, and displaying the second stitched image. In a ninth example of the method optionally including one or more of the first through eighth examples, the method further comprises receiving, from the trained neural network, probabilities for corresponding anatomy/views classified for plurality of images and the second plurality of images, determining whether the corresponding anatomy/views are correct based on an occurrence of anatomy/views and the probabilities, and adjusting a classification of an anatomy/view for a given image if one of the occurrence of anatomy/views and the probabilities indicate that the classification of the anatomy/view for the given image is incorrect.

In another representation, a method comprises controlling an x-ray source and an x-ray detector to acquire an image of a subject, classifying, with a trained neural network, an anatomy/view depicted in the image, performing post-processing of the image based on the anatomy/view, and displaying the post-processed image.

In a first example of the method, the method further comprises determining parameters for adjusting one or more of edge details, contrast, and noise level in the image according to the anatomy/view, and performing the post-processing of the image according to the determined parameters. In a second example of the method optionally including the first example, the method further comprises controlling the x-ray source and the x-ray detector to acquire a second image of the subject, wherein the first image and the second image depict adjacent and overlapping regions of the subject. In a third example of the method optionally including one or more of the first and second examples, the method further comprises classifying, with the trained neural network, a second anatomy/view depicted in the second image. In a fourth example of the method optionally including one or more of the first through third examples, performing the post-processing of the image based on the anatomy/view comprises registering the image to the second image according to the anatomy/view and the second anatomy/view, and stitching the image to the second image to generate a stitched image, and displaying the post-processed image comprises displaying the stitched image. In a fifth example of the method optionally including one or more of the first through fourth examples, the method further comprises adjusting contrast and performing noise reduction for the image and the second image according to the anatomy/view and the second anatomy/view, respectively, prior to registering the image to the second image. In a sixth example of the method optionally including one or more of the first through fifth examples, the method further comprises controlling the x-ray source and the x-ray detector to acquire a third image and a fourth image of the subject, wherein the first image and the second image depict adjacent and overlapping regions of the subject in a first view, and wherein the third image and the fourth image depict adjacent and overlapping regions of the subject in a second view different from the first view. In a seventh example of the method optionally including one or more of the first through sixth examples, the method further comprises classifying, with the trained neural network, a third anatomy/view depicted in the third image and a fourth anatomy/view depicted in the fourth image. In an eighth example of the method optionally including one or more of the first through seventh examples, the method further comprises registering the third image to the fourth image according to the third anatomy/view and the fourth anatomy/view, stitching the third image to the fourth image to generate a second stitched image with the second view, and displaying the second stitched image. In a ninth example of the method optionally including one or more of the first through eighth examples, the method further comprises receiving, from the trained neural network, probabilities for corresponding anatomy/views classified for the image, the second image, the third image, and the fourth image, and determining whether the corresponding anatomy/views are correct based on the probabilities prior to second probability, respectively.

In another embodiment, a method comprises acquiring one or more images of a subject, determining, from the one or more images of the subject with a classification network, an orientation and a position of the subject relative to an x-ray source and an x-ray detector, processing one or more x-ray images of the subject acquired with the x-ray source and the x-ray detector based on the orientation and the position of the subject, and displaying the one or more processed x-ray images.

In a first example of the method, acquiring the one or more images of the subject comprises acquiring, with an optical camera co-aligned with the x-ray source, the one or more images, and further comprising selecting one or more acquisition parameters based on the orientation and the position, and controlling the x-ray source and the x-ray detector according to the one or more acquisition parameters to acquire the one or more x-ray images. In a second example of the method optionally including the first example, the one or more images comprises the one or more x-ray images, and processing the one or more x-ray images comprises adjusting an appearance of the one or more x-ray images according to a view protocol selected based on the orientation and the position of the subject. In a third example of the method optionally including one or more of the first and second examples, the one or more x-ray images comprises a first plurality of x-ray images of the subject in a first orientation, and a second plurality of x-ray images of the subject in a second orientation, wherein determining the orientation with the classification network comprises determining the first orientation for the first plurality of x-ray images and the second orientation of the second plurality of x-ray images. In a fourth example of the method optionally including one or more of the first through third examples, processing the one or more x-ray images based on the orientation and position of the subject comprises registering and stitching the first plurality of x-ray images based on the first orientation into a first stitched image with a first field-of-view larger than each of the first plurality of x-ray images, and registering and stitching the second plurality of x-ray images based on the second orientation in to a second stitched image with a second field-of-view larger than each of the second plurality of x-ray images.

In yet another embodiment, an x-ray imaging system comprises an x-ray source for generating x-rays, an x-ray detector configured to detect the x-rays, a display device, and a processor configured with instructions in non-transitory memory that when executed cause the processor to: control the x-ray source and the x-ray detector to acquire an image of a subject; classify, with a trained neural network, an anatomy/view depicted in the image; perform post-processing of the image based on the anatomy/view; and display, via the display device, the post-processed image.

In a first example of the system, the processor is further configured with instructions in the non-transitory memory that when executed cause the processor to determine parameters for adjusting one or more of edge details, contrast, and noise level in the image according to the anatomy/view, and perform the post-processing of the image according to the determined parameters. In a second example of the system optionally including the first example, controlling the x-ray source and the x-ray detector to acquire the image comprises controlling the x-ray source and the x-ray detector to acquire a plurality of images of the subject, and classifying the anatomy/view depicted in the image comprises classifying, with the trained neural network, an anatomy/view depicted in each image of the plurality of images. In a third example of the system optionally including one or more of the first and second examples, the processor is further configured with instructions in the non-transitory memory that when executed cause the processor to determine a first plurality of images in the plurality of images corresponding to a first view, determine a second plurality of images in the plurality of images corresponding to a second view, register and stitch the first plurality of images into a first stitched image according to the first view, and register and stitch the second plurality of images into a second stitched image according to the second view. In a fourth example of the system optionally including one or more of the first through third examples, the system further comprises an optical camera positioned adjacent to the x-ray source and co-aligned with the x-ray source, wherein the processor is further configured with instructions in the non-transitory memory that when executed cause the processor to: acquire camera data via the optical camera; classify, with the trained neural network, an anatomy/view of the subject depicted in the camera data; select one or more acquisition parameters based on the anatomy/view of the subject depicted in the camera data; and control the x-ray source and the x-ray detector with the one or more acquisition parameters to acquire the image of the subject.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
controlling an x-ray source and an x-ray detector to acquire a plurality of images of a subject;
classifying, with a trained neural network, a respective anatomy/view depicted in each image of the plurality of images, where each respective anatomy/view includes a predicted anatomy and a predicted view depicted in that image;
performing post-processing of each image based on the respective anatomy/view, including selecting two or more images from the plurality of images that are classified as having the same predicted view and stitching the two or more images to form a stitched image; and
displaying the stitched image.

2. The method of claim 1, further comprising determining parameters for adjusting one or more of edge details, contrast, and noise level in each image according to the respective anatomy/view, and performing the post-processing of the image according to the determined parameters.

3. The method of claim 1, wherein the predicted view is a first predicted view, and further comprising:
determining, based on the respective anatomy/view depicted in each image of the plurality of images, that the plurality of images further includes two or more additional images classified as having a second predicted view, different than the first predicted view;
stitching together the two or more additional images to form a second stitched image; and
displaying the second stitched image.

4. The method of claim 1, wherein the at least two images include a first image and a second image that depict adjacent and overlapping regions of the subject, and wherein classifying, with the trained neural network, the respective anatomy/view depicted in each image of the plurality of images includes classifying at least a first anatomy/view depicted in the first image and a second anatomy/view depicted in the second image.

5. The method of claim 4, wherein performing the post-processing comprises registering the plurality of images according to the anatomy/views depicted in the plurality of images, including registering the first image to the second image according to the first anatomy/view and the second anatomy/view, and stitching the registered first image and second image to generate the stitched image.

6. The method of claim 5, wherein stitching the first image and the second image comprises stitching the first image and the second image according to an image pasting protocol configured for the predicted view of the first image and the second image.

7. The method of claim 6, further comprising controlling the x-ray source and the x-ray detector to acquire a second plurality of images including at least a third image and a fourth image of the subject, wherein the plurality of images including the first image and the second image depict adjacent and overlapping regions of the subject in a first view, and wherein the second plurality of images depict adjacent and overlapping regions of the subject in a second view different from the first view.

8. The method of claim 7, further comprising classifying, with the trained neural network, a respective anatomy/view depicted in each image of the second plurality of images including a third anatomy/view depicted in the third image and a fourth anatomy/view depicted in the fourth image.

9. The method of claim 8, further comprising determining that the respective anatomy/view depicted in each image of the second plurality of images includes the second view, registering the second plurality of images according to an image pasting protocol for the second view, stitching the registered second plurality of images to generate a second stitched image with the second view, and displaying the second stitched image.

10. The method of claim 9, further comprising receiving, from the trained neural network, probabilities for corresponding anatomy/views classified for the plurality of images and the second plurality of images, determining whether the corresponding anatomy/views are correct based on an occurrence of anatomy/views and the probabilities, and adjusting a classification of an anatomy/view for a given image if one of the occurrence of anatomy/views and the probabilities indicate that the classification of the anatomy/view for the given image is incorrect.

11. An x-ray imaging system, comprising:
an x-ray source for generating x-rays;
an x-ray detector configured to detect the x-rays;
a display device; and
a processor configured with instructions in non-transitory memory that when executed cause the processor to:
control the x-ray source and the x-ray detector to acquire a plurality of images of a subject;
classify, with a trained neural network, a respective anatomy/view depicted in each image of the plurality of images;
receiving, from the trained neural network, a respective probability for each anatomy/view classified for the plurality of images, determining whether each anatomy/view is correct based on an occurrence of anatomy/views and each probability, and adjusting a classification of an anatomy/view for a given image if one of the occurrence of anatomy/views and the probabilities indicate that the classification of the anatomy/view for the given image is incorrect;
perform post-processing of each image based on each anatomy/view; and
display, via the display device, the post-processed image.

12. The system of claim 11, wherein the processor is further configured with instructions in the non-transitory memory that when executed cause the processor to determine parameters for adjusting one or more of edge details, contrast, and noise level in each image according to the respective anatomy/view, and perform the post-processing of each image according to the determined parameters.

13. The system of claim 11, wherein the processor is further configured with instructions in the non-transitory memory that when executed cause the processor to determine a first plurality of images in the plurality of images corresponding to a first view, determine a second plurality of images in the plurality of images corresponding to a second view, register and stitch the first plurality of images into a first stitched image according to the first view, and register and stitch the second plurality of images into a second stitched image according to the second view.

14. The system of claim 11, further comprising an optical camera positioned adjacent to the x-ray source and co-aligned with the x-ray source, wherein the processor is further configured with instructions in the non-transitory memory that when executed cause the processor to:
acquire camera data via the optical camera;
classify, with the trained neural network, an anatomy/view of the subject depicted in the camera data;
select one or more acquisition parameters based on the anatomy/view of the subject depicted in the camera data; and
control the x-ray source and the x-ray detector with the one or more acquisition parameters to acquire the plurality of images of the subject.

* * * * *